(12) United States Patent
Chen

(10) Patent No.: US 6,622,571 B2
(45) Date of Patent: Sep. 23, 2003

(54) APPARATUS FOR MEASURING TENSION AND STRESS CAPABLE OF ADJUSTING AN ANGLE OF MEASUREMENT

(75) Inventor: Yi-Jen Chen, Taipei (TW)

(73) Assignee: Asustek Computer Inc., Taipei (TW)

( * ) Notice: Subject to any disclaimer, the term of this patent is extended or adjusted under 35 U.S.C. 154(b) by 0 days.

(21) Appl. No.: 09/968,877

(22) Filed: Oct. 3, 2001

(65) Prior Publication Data

US 2002/0040606 A1 Apr. 11, 2002

(30) Foreign Application Priority Data

Oct. 9, 2000 (TW) .......................................... 89217546

(51) Int. Cl.[7] ................................................ G01N 3/08
(52) U.S. Cl. ............................. 73/831; 73/856; 73/826
(58) Field of Search ......................... 73/831, 856, 826, 73/847, 854, 857, 858, 859, 860

(56) References Cited

U.S. PATENT DOCUMENTS 5,005,424 A * 4/1991 Markowski .................. 73/834
5,576,478 A * 11/1996 Brungraber ...................... 73/9
6,142,010 A * 11/2000 Merck et al. .................. 73/81

* cited by examiner

Primary Examiner—Edward Lefkowitz
Assistant Examiner—Corey D. Mack
(74) Attorney, Agent, or Firm—Rabin & Berdo, PC

(57) ABSTRACT

An apparatus for measuring tension and stress, which is capable of adjusting an angle of measurement. The apparatus includes a base plate, a supporting member, and a body for measuring tension and stress. The supporting member is mounted on the base plate. The supporting member further includes a revolving spindle supported by a bearing so that the body for measuring tension and stress can be attached to the supporting member in a way that the body for measuring tension and stress is capable of turning on the revolving spindle. In this way, the user can adjust the angle between the body for measuring tension and stress and the base plate, fulfilling the purpose of doing measurement for an object in an arbitrary angle of measurement.

3 Claims, 6 Drawing Sheets

APPARATUS FOR MEASURING TENSION AND STRESS CAPABLE OF ADJUSTING AN ANGLE OF MEASUREMENT

BACKGROUND OF THE INVENTION

This application incorporates by reference Taiwanese application Serial No. 89217546, filed on Oct. 9, 2000.

1. Field of the Invention

The invention relates in general to an apparatus for measuring tension and stress, and more particularly to an apparatus for measuring tension and stress, which is capable of adjusting an angle of measurement.

2. Description of the Related Art

Tension and stress testers are employed in measurement of tension and/or stress in different ways, or of a relationship between tension/stress and strain in different kinds of objects, such as the measurement of elastic force and coefficient of elasticity of a spring, the tension between two magnets, and static and dynamic friction of an object.

By the angle of measurement, conventional tension and stress testers can be categorized into the testers for measurement in a horizontal direction and testers for measurement in vertical direction. FIGS. 1–1B respectively illustrate a top view and side view of a conventional horizontal tension and stress tester for measurement in the horizontal direction. The horizontal tension and stress tester 100 has an elongated configuration along the Y-axis. In the horizontal tension and stress tester 100, a carriage 106 is mounted on a sleeve bearing 108, where the sleeve bearing 108 is relatively supported by a guide shaft 110. Further, a spiral shaft 104 goes through and relatively supports the carriage 106. In this way, by driving the spiral shaft 110 using a motor 102, the carriage 106 can move along the guide shaft 110 in the Y-axis. On the other hand, the carriage 106 further includes a tension and stress sensor 112 for measuring tension and stress on an object being tested (not shown in Figures). Thus, the motor 112 controls the displacement of the tension and stress sensor 112 mounted on the carriage 106.

In order to employ the horizontal tension and stress tester 100 to measure tension and/or stress in different ways, or to measure a relationship between tension/stress and strain in different kinds of objects, the tension and stress sensor 112 can be additionally equipped with a suitable test tool for measurement, taken along the Y-axis, of an object to be tested in the supporting frame (not shown).

FIGS. 2A and 2B, corresponding to FIGS. 1A and 1B, respectively illustrate a front view and side view of a conventional vertical tension and stress tester 200 for measurement in a vertical direction. The vertical tension and stress tester 200 is mounted on a base plate 202, and has an elongated configuration along the Z-axis. The vertical tension and stress tester 200 has a tension and stress sensor 204 capable of moving along the Z-axis and measuring tension and/or stress of an object being tested in the direction along the Z-axis. Since the mechanism and operation of the vertical tension and stress tester 200 are identical to that of the horizontal tension and stress tester 100 except for the angle of measurement, for the sake of brevity, they will not be described.

As described above, the horizontal tension and stress tester 100 can only do measurements for the object horizontally while the vertical tension and stress tester 200 can only do measurements for the object vertically. When it is required to do measurements for the object in the horizontal and vertical directions respectively, both the horizontal tension and stress tester 100 and the vertical tension and stress tester 200 should be employed. However, if purchase of the two testers is necessary, the total cost of testing is greatly increased. Besides, when the object is required to be tested in an arbitrary angle of measurement, the two testers are ineffective, leading to a limitation in the required measurement.

SUMMARY OF THE INVENTION

It is therefore an object of the invention to provide an apparatus for measuring tension and stress capable of adjusting an angle of measurement. By using the apparatus for measuring tension and stress according to the invention, tension and stress measurement for an object can be done in an arbitrary angle of measurement. When the object is required to be tested in both horizontal and vertical directions, the apparatus for measuring tension and stress according to the invention can fulfil this requirement. Thus, it is unnecessary to employ two different tension and stress testers for measurement, resulting in the expense for measuring instrument reduced by about ¼ to ½ as compared with the expense of the conventional approach. Hence, the total cost for measurement is reduced greatly. In addition, the apparatus for measuring tension and stress according to the invention is more convenient to users than the conventional approach does.

In accordance with the object of the invention, it provides an apparatus for measuring tension and stress. The apparatus includes a base plate, a supporting member, and a body for measuring tension and stress. The supporting member is mounted on the base plate. The body for measuring tension and stress is attached to the supporting member so that the body for measuring tension and stress is capable of being turned, and capable of being secured on the supporting member after the body for measuring tension and stress makes an angle with the base plate for measurement.

For adjusting the angle with the base plate for measurement, the supporting member includes a revolving spindle with a bearing for attaching the body for measuring tension and stress to the supporting member, and for the body for measuring tension and stress to turn on the revolving spindle for adjusting the angle with the base plate for measurement.

In addition, the body for measuring tension and stress includes a tension and stress sensor, a translational mechanism, and a range finder. The tension and stress sensor is used for measuring tension and/or stress of an object to be tested. The translational mechanism is employed for driving the tension and stress sensor in translation. The range finder is used for measuring a distance between the object and the range finder.

BRIEF DESCRIPTION OF THE DRAWINGS

Other objects, features, and advantages of the invention will become apparent from the following detailed description of the preferred but non-limiting embodiments. The description is made with reference to the accompanying drawings, in which.

DETAILED DESCRIPTION OF THE INVENTION

Figure 1A:
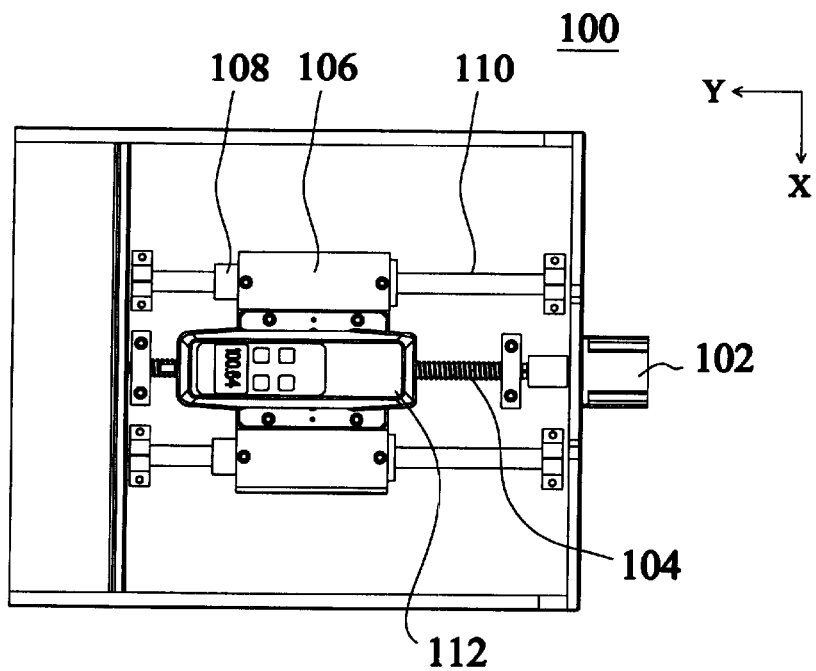
FIGS. 1A and 1B respectively illustrate a top view and side view of a conventional horizontal tension and stress tester for measurement in horizontal direction.
Figure 1B:
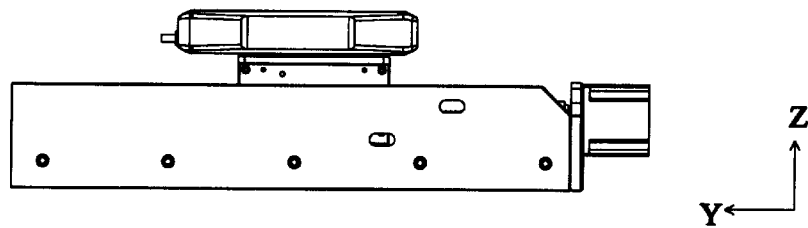
Figures 2A, 2B:
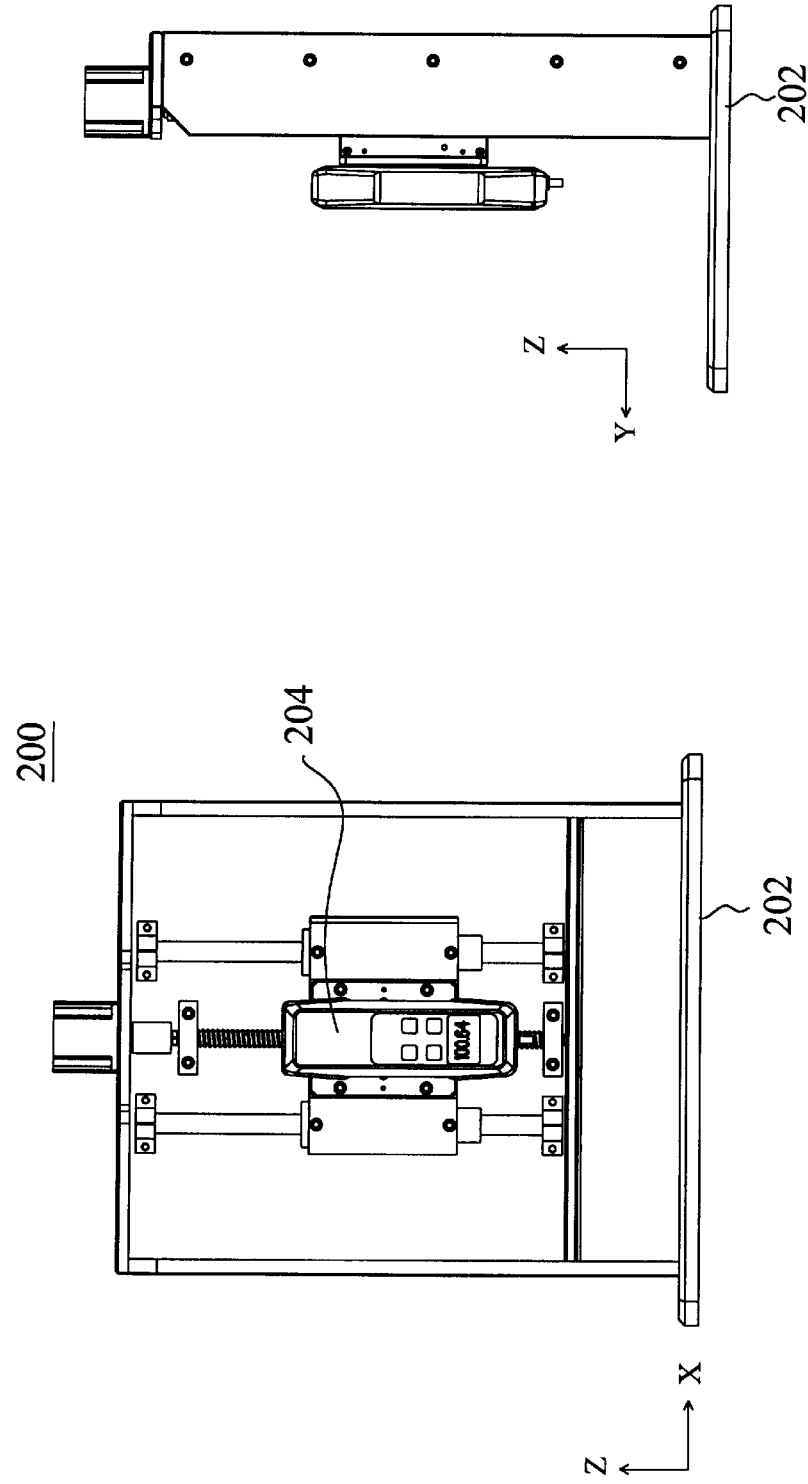
FIGS. 2A and 2B respectively illustrate a front view and side view of a conventional vertical tension and stress tester for measurement in vertical direction.
Figure 3:
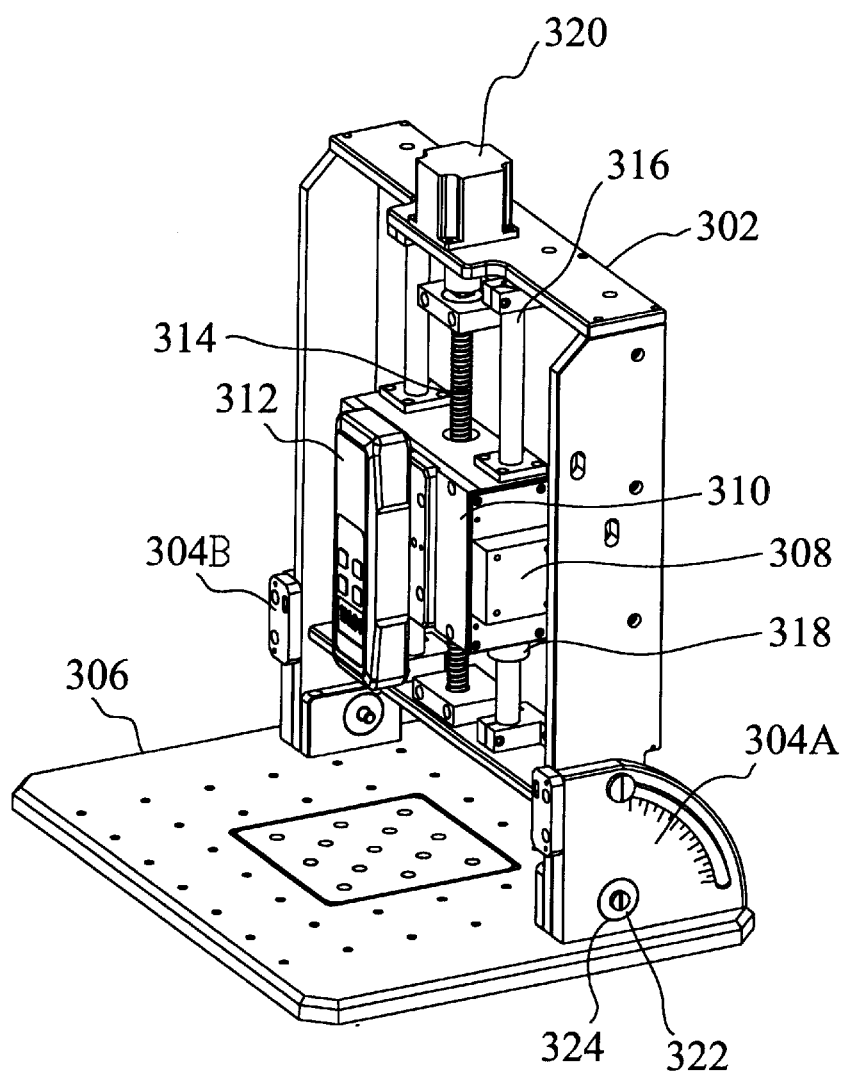
FIG. 3 is a perspective view of an apparatus for measuring tension and stress, which is capable of adjusting the angle of measurement, according to a preferred embodiment of the invention.

FIG. 3 illustrates a perspective view of the apparatus for measuring tension and stress, which is adapted for adjusting the angle of measurement. The apparatus for measuring tension and stress 300 includes a body for measuring tension and stress 302, a supporting member 304, and a base plate 306. The body for measuring tension tension and stress is adjusted to a position perpendicular to the base plate; and stress 302 includes a tension and stress sensor 312, a translational mechanism, and a range finder 308. The tension and stress sensor 312 is used for measuring tension and stress on an object to be tested (not shown). The translational mechanism is used for driving the tension and stress sensor 312. The range finder 308 is used for measuring the distance between the object being tested and the range finder 308. The supporting member 304 is mounted on the base plate 306.

The translational mechanism includes a carriage 310, a spiral shaft 314, a guide shaft 316, a sleeve bearing 318, and a motor 320. The carriage 310 has the tension and stress sensor 312 mounted thereon. The carriage 310 is attached to the sleeve bearing 318 through which the carriage 310 is relatively supported by the guide shaft 316. In addition, the carriage 310 is coupled to the spiral shaft 314. By using the motor 320, the spiral shaft 314 rotates and leads to the linear motion of the carriage 310 along the direction of the guide shaft 316.

The apparatus for measuring tension and stress according to the invention has a feature that the supporting member 304, which is mounted on the base plate 306, includes a revolving spindle 322 and a bearing 324, for the attachment of the body for measuring tension and stress to the supporting member 304. Due to the attachment relationship to the supporting member 304, the body for measuring tension and stress 302 can be turned on the revolving spindle 322. Hence, the angle between the body for measuring tension and stress 302 and the base plate 306 is adjustable, and the body for measuring tension and stress 302 can then be secured at an arbitrary angle with the base plate 306 for the requirement of various angles of measurement. In FIG. 3, it illustrates the apparatus for measuring tension and stress having two supporting members 304A and 304B.

Figure 4:
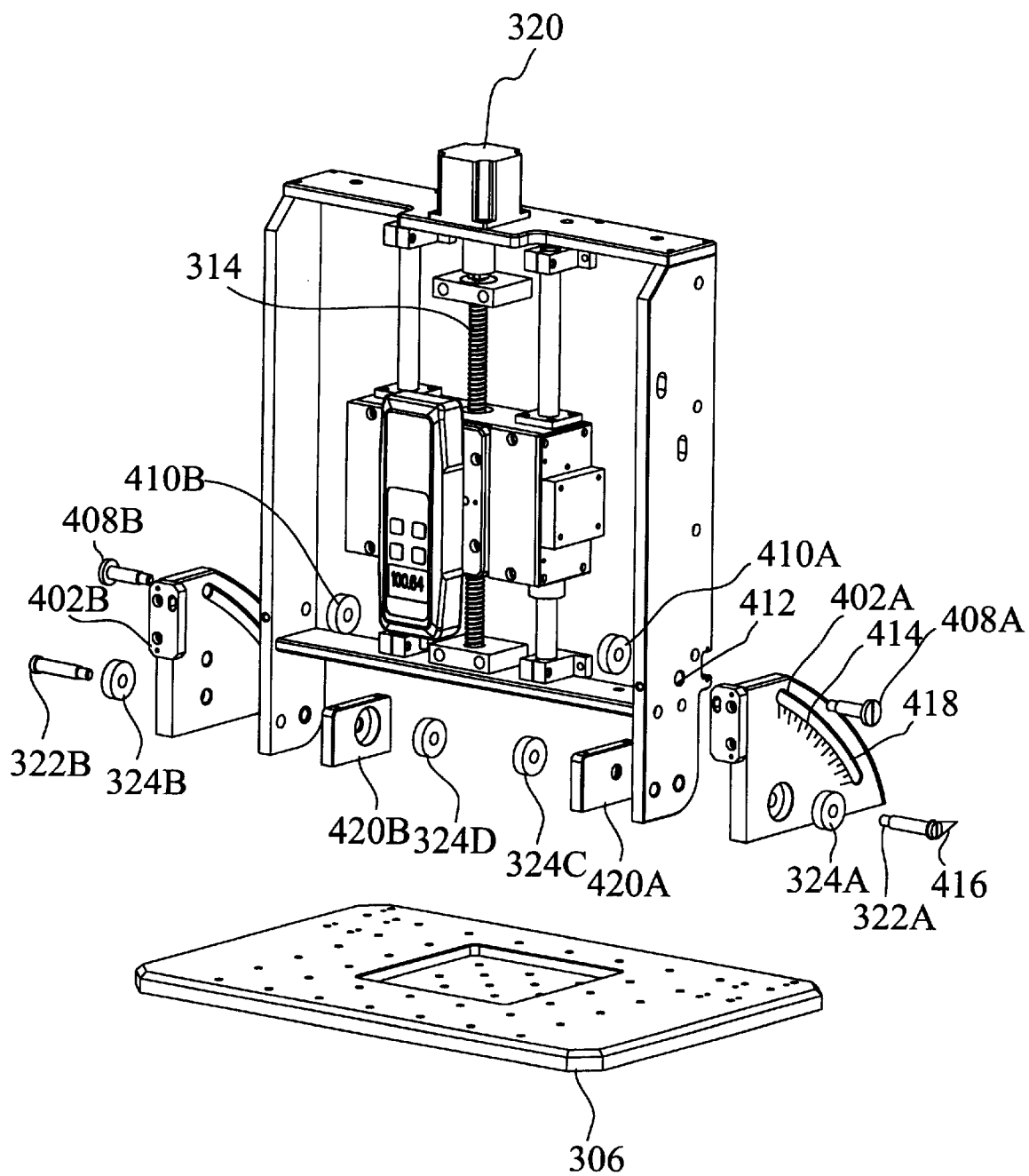
FIG. 4 is an exploded view of the apparatus for measuring tension and stress as shown in FIG. 3.

Referring to FIG. 4, the supporting member 304 further includes a supporting frame 402, a bolt 408, and a nut 410 as well as the revolving spindle 322 and bearing 324. The revolving spindle 322 and bearing 324 are used for attaching the body for measuring tension and stress 302 to the supporting frame 402. Through an arc opening 418 of the supporting frame 402, the bolt 408 is fixed to the body for measuring tension and stress 302. The bolt 408 is to be fastened with the nut 410 so that the body for measuring tension and stress 302 is fixed precisely.

FIG. 4 illustrates the apparatus for measuring tension and stress having two A revolving spindles 322A and 322B, four bearings 324A, 324B, 3240, and 324D, two supporting frame 402A and 402B, two bolts 408A and 408B, and two nuts 410A and 410B. In addition, the apparatus for measuring tension and stress further employs two supporting partitions 420A and 420B for separating the body for measuring tension and stress 302 and bearings 3240 and 324D.

Referring to FIGS. 3 and 4, the body for measuring tension and stress 302 is capable of turning on the revolving spindle 322 as the pivot. In this way, a user can turn the body for measuring tension and stress 302, making a certain angle with the base plate 306. Next, inserting the bolt 408 through the arc opening 418 of the supporting frame 402 into a corresponding hole 412 of the body for measuring tension and stress 302 and then fastening the bolt 408, one can initially fasten the body for measuring tension and stress 302.

In addition, the supporting frame 402 further includes graduations 414 disposed along the arc opening 418, and the revolving spindle 322 further includes an indicator hand 416. In this way, when the user turns the body for measuring tension and stress 302, the indicator hand 416 is turned as well. Thus, by using the graduations 414 and the indicator hand 416, the angle of measurement is accurately indicated so that the user can adjust the angle of measurement for the requirements for measurement precisely. In addition, by the effect of the bearing 324, the adjustment of the angle of measurement is effortless.

In the course of measurement, by using the tension and stress sensor 312 to measure the tension/stress of the object and using the range finder 308 to measure distance between the object and the range finder 308, the relationship of the tension/stress and the distance can be obtained. For the relationship obtained, the precision depends on the precision of the spiral shaft 314, motor 320, the tension and stress sensor 312, and the range finder 308.

Preferably, for high precision of measurement, the apparatus for measuring tension and stress employs a precise ball spiral shaft, a micro-stepping motor, a tension and stress sensor with digital display, and a laser range finder as the spiral shaft 314, the motor 320, the tension and stress sensor 312, and the range finder 308 respectively. In this way, the measurement of the apparatus for measuring tension and stress according to the invention can be done with the precision of $10^{-4}$ mm.

Figure 5A:
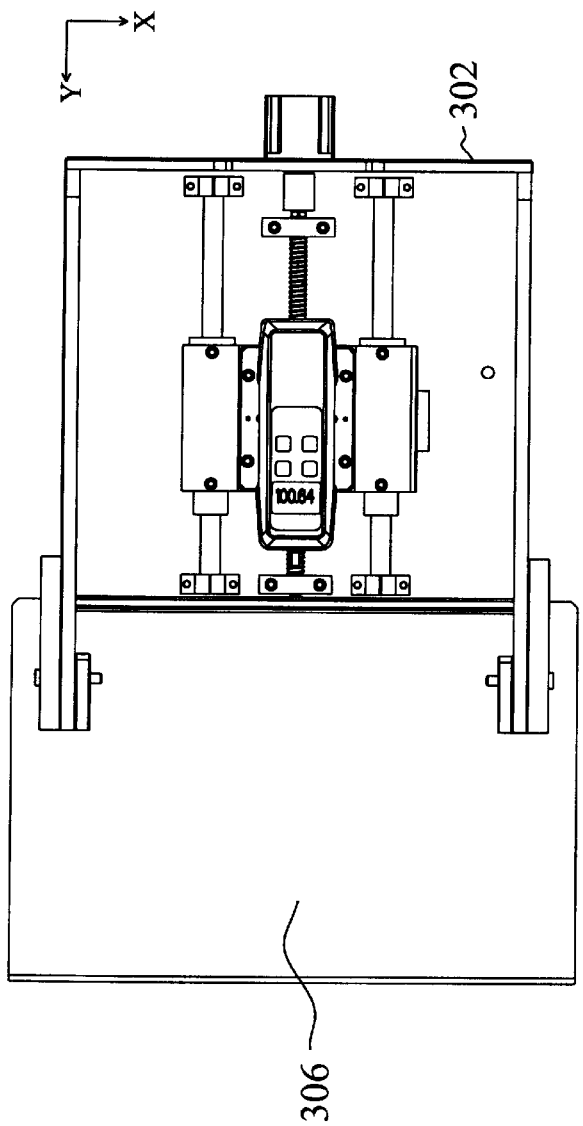
FIGS. 5A and 5B are respectively a top view and side view of the apparatus for measuring tension and stress as shown in FIG. 3 when the body for measuring tension and stress is adjusted to a position parallel to the base plate.
Figure 5B:
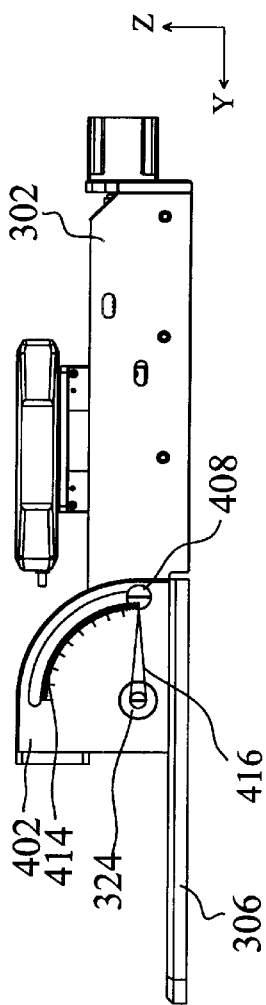

FIGS. 5A and 5B respectively illustrate a top view and a side view of the apparatus for measuring tension and stress shown in FIG. 3 when the body for measuring tension and stress 302 is secured in a position parallel to the base plate 306. When the measurement of the object is necessary to be done horizontally, the body for measuring tension and stress 302 is to be turned on the revolving spindle 322 as the pivot so that the body for measuring tension and stress 302 is parallel to the base plate 306. While the body for measuring tension and stress 302 is turned on the pivot, the indicator hand 416 is turned on the pivot at the same time, indicating a turning angle of the body for measuring tension and stress 302 in the graduations 414. Thus, by using the indicator hand 414 and graduations 416, the user can precisely adjust the turning angle.

Figure 6B:
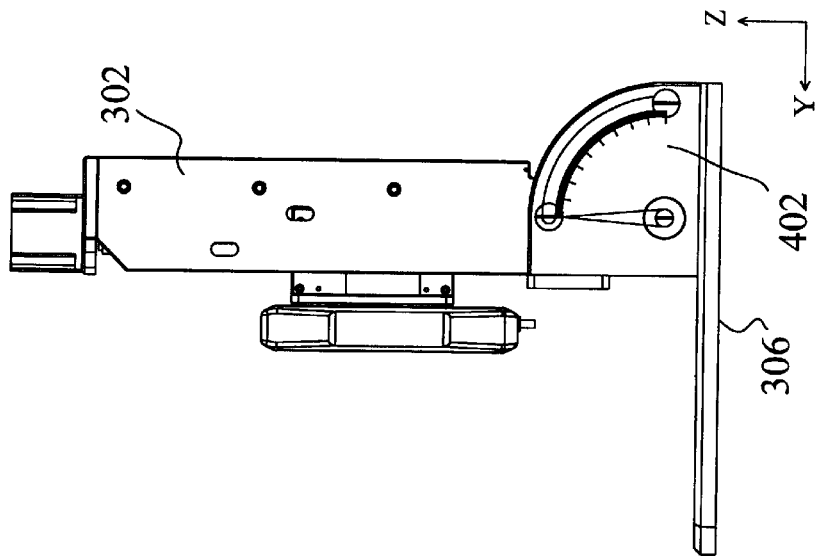
FIGS. 6A and 6B are respectively a front view and side view of the apparatus for measuring tension and stress as shown in FIG. 3 when the body for measuring
Figure 6A:
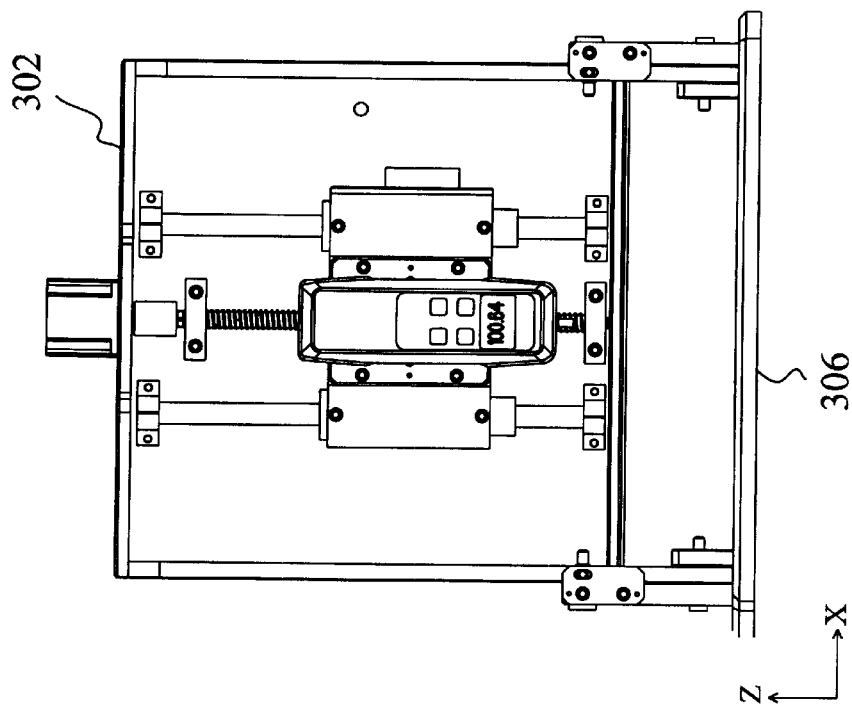

FIGS. 6A and 6B respectively illustrate a front view and a side view of the apparatus for measuring tension and stress shown in FIG. 3 when the body for measuring tension and stress 302 is secured in a position perpendicular to the base plate 306. When the measurement of the object is necessary to be done vertically, the body for measuring tension and stress 302 is to be turned on the revolving spindle 322 as the pivot so that the body for measuring tension and stress 302 is perpendicular to the base plate 306. While the body for measuring tension and stress 302 is turned on the pivot, the indicator hand 416 is turned on the pivot at the same time, indicating a turning angle of the body for measuring tension and stress 302 in the graduations 414. Thus, by using the indicator hand 414 and graduations 416, the user can precisely adjust the turning angle.

As can be seen from the above, the measurement in horizontal and vertical directions can be done with only the apparatus for measuring tension and stress according to the invention. In this way, the total cost of measurement instrument is reduced by about ¼ to ½ as compared with the conventional approach that two tension and stress testers (including the horizontal and vertical testers) are employed. In addition, the turning angle of the body for measuring tension and stress, i.e. the angle of measurement, is adjustable so that measurement can be done with an arbitrary angle of measurement. For the users, the apparatus for measuring tension and stress according to the invention is more convenient than the conventional tension and stress testers.

While the invention has been described by way of example and in terms of a preferred embodiment, it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. An apparatus for measuring tension and stress, comprising:
    a base plate;
    a supporting member mounted on the base plate; and
    a body for measuring tension and stress, and being pivotally attached to the supporting member so that said body is positional at a plurality of different a positions relative to said base plate and so that at each of the different positions, said body and said base plate collectively form a different angle therebetween, and being securable to the supporting member to retain said body in any one of the different positions,
    wherein said body is pivotal so that at one of the different positions, said body is essentially perpendicular to said base plate, and at another one of the different positions, said body is essentially parallel to said base plate,
    wherein when said body is essentially perpendicular to said base plate, said apparatus is adapted to perform vertical measurements on a sample, and when said body is essentially parallel to said base plate, said apparatus is adapted to perform horizontal measurements on a sample and
    wherein the supporting member comprises a revolving spindle with a bearing for attaching the body for measuring tension and stress to the supporting member, the body for measuring tension and stress being turnable on the revolving spindle for adjusting the angle between the body and the base plate.

2. An apparatus for measuring tension and stress, comprising:
    a base plate;
    a supporting member mounted on the base plate; and
    a body for measuring tension and stress, and being pivotally attached to the supporting member so that said body is positional at a plurality of different positions relative to said base plate and so that at each of the different positions, said body and said base plate collectively form a different angle therebetween, and being securable to the supporting member to retain said body in any one of the different positions,
    wherein said body is pivotal so that at one of the different positions, said body is essentially perpendicular to said base plate, and at another one of the different positions, said body is essentially parallel to said base plate,
    wherein when said body is essentially perpendicular to said base plate, said apparatus is adapted to perform vertical measurements on a sample, and when said body is essentially parallel to said base plate, said apparatus is adapted to perform horizontal measurements on a sample,
    wherein said body comprises:
        a tension and stress sensor for measuring tension and/or stress of an object to be tested;
        a translational mechanism for driving the tension and stress sensor in translation; and
        a range finder for measuring a distance between the object and the range finder, and
    wherein the translational mechanism comprises:
        a motor; and
        a sliding carriage having the tension and stress sensor thereon, the sliding carriage being attached to a guide shaft through a sleeve bearing, and the sliding carriage being attached to a spiral shaft, wherein the spiral shaft is driven by the motor so that the sliding carriage performs translation motion.

3. An apparatus for measuring tension and stress, comprising:
    a base plate;
    a supporting member mounted on the base plate; and
    a body for measuring tension and stress, and being pivotally attached to the supporting member so that said body is positional at a plurality of different positions relative to said base plate and so that at each of the different positions, said body and said base plate collectively form a different angle therebetween, and being securable to the supporting member to retain said body in any one of the different positions,
    wherein said body is pivotal so that at one of the different positions, said body is essentially perpendicular to said base plate, and at another one of the different positions, said body is essentially parallel to said base plate,
    wherein when said body is essentially perpendicular to said base plate, said apparatus is adapted to perform vertical measurements on a sample, and when said body is essentially parallel to said base plate, said apparatus is adapted to perform horizontal measurements on a sample,
    wherein the supporting member comprises a revolving spindle with a bearing for attaching the body for measuring tension and stress to the supporting member, the body for measuring tension and stress being turnable on the revolving spindle for adjusting the angle between the body and the base plate,
    wherein the supporting member further comprises a supporting fame, to which the body for measuring tension and stress is attached by using the revolving spindle and the bearing, and
    wherein the supporting frame comprises an arc opening and a bolt, where the body for measuring tension and stress is fastened to the supporting member by fastening the bolt through the arc opening.

\* \* \* \* \*